(12) United States Patent
Walter et al.

(10) Patent No.: US 7,737,301 B2
(45) Date of Patent: Jun. 15, 2010

(54) PROCESS FOR THE PRODUCTION OF ANILINES

(75) Inventors: Harald Walter, Basel (CH); Camilla Corsi, Basel (CH); Josef Ehrenfreund, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/065,304

(22) PCT Filed: Aug. 28, 2006

(86) PCT No.: PCT/EP2006/008398

§ 371 (c)(1),
(2), (4) Date: Aug. 7, 2008

(87) PCT Pub. No.: WO2007/025693

PCT Pub. Date: Mar. 8, 2007

(65) Prior Publication Data

US 2009/0221855 A1    Sep. 3, 2009

(30) Foreign Application Priority Data

Aug. 30, 2005   (CH) ..................... 1416/05

(51) Int. Cl.
*C07C 209/62*  (2006.01)
*C07C 209/10*  (2006.01)
*C07C 211/45*  (2006.01)
*C07C 211/48*  (2006.01)

(52) U.S. Cl. ...................... 564/307; 564/415

(58) Field of Classification Search ........................ None
See application file for complete search history.

(56) References Cited

U.S. PATENT DOCUMENTS

2005/0221989 A1   10/2005  Walter et al.

FOREIGN PATENT DOCUMENTS

| WO | 03/074491 | 9/2003 |
|----|-----------|--------|
| WO | 2006/061226 | 6/2006 |

OTHER PUBLICATIONS

Noriyasu Katoaka et al: "Air Stable, Sterically Hindered Ferrcenyl Dialkylphosphines for Palladium-Catalyzed C-C, C-N, and C-O Bond-Forming Cross-Coupling", Journal of Organic Chemistry, American Chemical Society. Easton, US, vol. 67, Jul. 4, 2002, pp. 5553-5566.

*Primary Examiner*—Brian J Davis
(74) *Attorney, Agent, or Firm*—William F. Mulholland, II

(57) ABSTRACT

The present invention relates to a process for the preparation of compounds of formula wherein $R_1$, $R_2$ and $R_3$ are each independently of the others hydrogen or $C_1$-$C_4$alkyl, by a) reacting compounds of formula (II) wherein $R_1$, $R_2$ and $R_3$ are as defined for formula (I) and X is bromine or chlorine, with a compound of formula (III) wherein $R_4$ is hydrogen or $C_1$-$C_4$alkyl, in the presence of a base and catalytic amounts of at least one palladium complex compound, to form compounds of formula (IV) wherein $R_1$, $R_2$, $R_3$ and $R_4$ are as defined for formula (I), and b) converting those compounds, using a reducing agent, into compounds of formula (I).

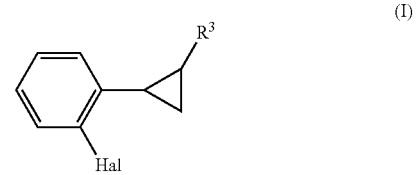

(I)

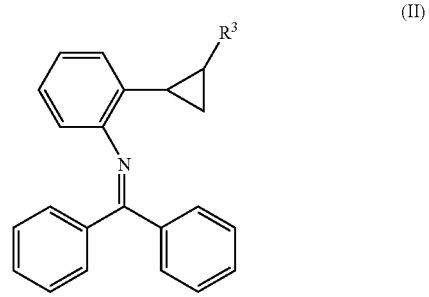

(II)

(III)

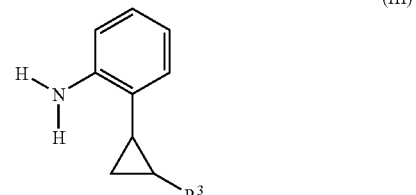

(IV)

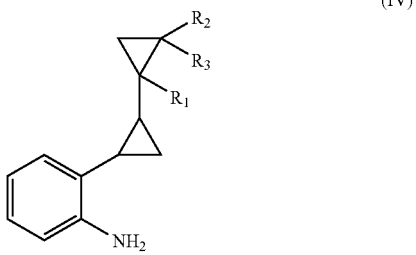

12 Claims, No Drawings

PROCESS FOR THE PRODUCTION OF ANILINES

This application is a National Stage Entry under 35 USC §371 of International application serial number PCT/EP2006/008398, filed on Aug. 28, 2006, which claims priority to CH 1416/05, filed on Aug. 30, 2005, the contents of which are incorporated herein by reference.

The present invention relates to a process for the amination of ortho-bicyclopropyl-substituted halobenzenes and also to intermediates of that process.

Ortho-bicyclopropyl-substituted primary anilines such as, for example, 2-bicyclopropyl-2-yl-phenylamine are valuable intermediates for the preparation of fungicides such as those described, for example, in WO 03/074491.

In general terms, anilines can be prepared from halobenzenes by means of palladium-catalysed cross-coupling reactions. Such palladium-catalysed cross-coupling reactions are described in the following summary articles: Handbook of Organopalladium Chemistry for Organic Synthesis, Vol. 1, 1051-1096, 2002; Journal of Organometallic Chemistry, 576, 125-146, 1999 and Journal of Organometallic Chemistry, 653, 69-82, 2002. The basic disadvantage of palladium-catalysed cross-coupling is that direct preparation of primary anilines is not possible.

Therefore, when using palladium-catalysed cross-coupling, primary anilines have to prepared from the corresponding halobenzenes in synthesis procedures comprising at least two stages.

Such a two-stage process for the preparation of ortho-bicyclopropyl-substituted primary anilines, using imines as nucleophiles, is described in WO 03/074491 (see Scheme 1).

Scheme 1:

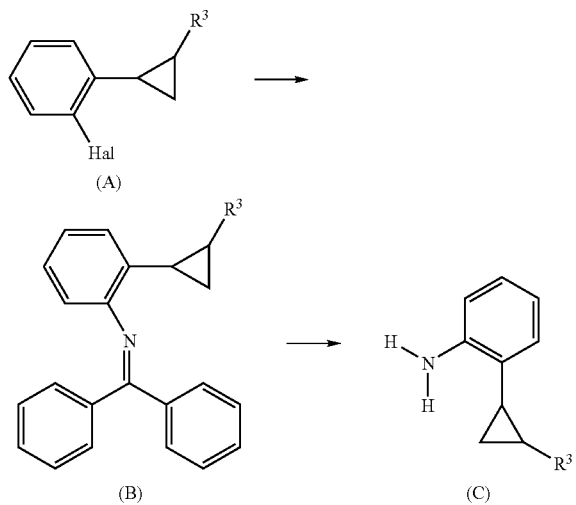

According to WO 03/074491, substituted 2-(2-halophenyl)cyclopropanes of formula (A), wherein Hal is bromine or iodine and $R^3$ is, inter alia, unsubstituted or substituted cyclopropyl, are aminated in a two-stage reaction to form the corresponding 2-(2-aminophenyl)cyclopropanes (C). For that purpose, firstly benzophenoneimine, sodium tert-butanolate, tris(dibenzylidene-acetone)dipalladium ($Pd_2dba_3$) and racemic 2,2'-bis(diphenylphosphine)-1,1'-binaphthyl ("BINAP") are added. In the second reaction step, the resulting imines (B) are reacted with, for example, hydroxylamine and sodium acetate to form the corresponding 2-(2-aminophenyl) bicyclopropanes (C). As a further palladium ligand, 1,1'-bis(diphenylphosphino)ferrocene ("dppf") is proposed in WO 03/074491.

This reaction procedure is described in WO 03/074491 exclusively for bromo- or iodo-benzenes, not for chlorobenzenes. It has been found that the reaction procedure described in WO 03/074491 is poorly suited to the imination of the less reactive but more economically priced 2-(2-chlorophenyl)cyclopropanes in high yields.

The reaction procedure described in WO 03/074491 for the preparation of primary anilines is not suitable for the large-scale preparation of ortho-bicyclopropyl-substituted primary anilines because of the high cost of the benzophenoneimine.

The problem of the present invention is accordingly to provide a new process for the preparation of ortho-bicyclopropyl-substituted primary anilines which avoids the above-mentioned disadvantages of the known process and makes it possible to prepare those compounds at economically reasonable cost and in easily manageable manner in high yields and good quality.

The present invention accordingly relates to a process for the preparation of compounds of formula I

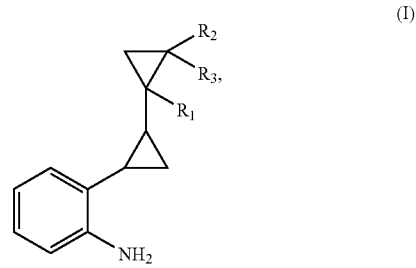

wherein $R_1$, $R_2$ and $R_3$ are each independently of the others hydrogen or $C_1$-$C_4$alkyl, which process comprises a) reacting a compound of formula II

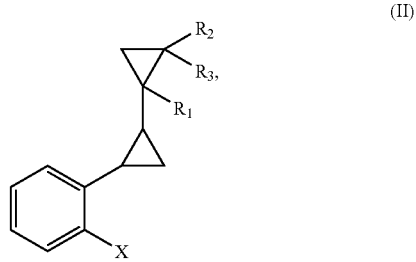

wherein $R_1$, $R_2$ and $R_3$ are as defined for formula I and X is bromine or chlorine, with a compound of formula III

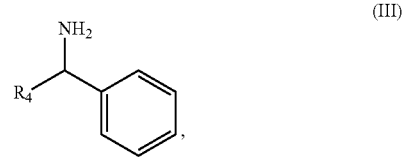

wherein $R_4$ is hydrogen or $C_1$-$C_4$alkyl, in the presence of a base and catalytic amounts of at least one palladium complex compound, to form a compound of formula IV

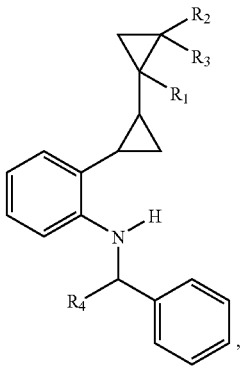

(IV)

wherein $R_1$, $R_2$, $R_3$ and $R_4$ are each independently of the others hydrogen or $C_1$-$C_4$alkyl; and b) converting that compound, using a reducing agent, into the compound of formula I.

Compounds of formula I occur in various stereoisomeric forms, which are described in formulae $I_I$, $I_{II}$, $I_{III}$ and $I_{IV}$:

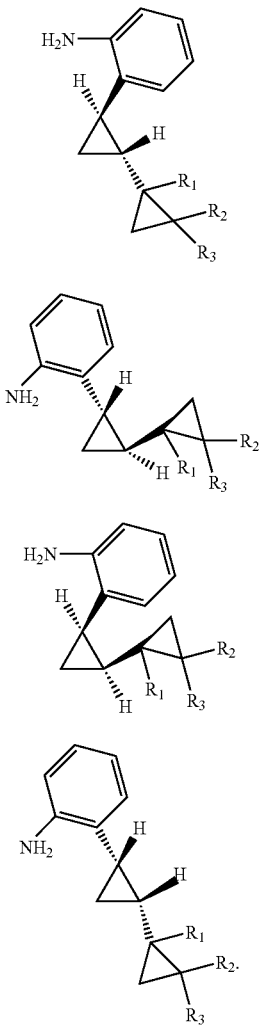

The process according to the invention includes the preparation of those stereoisomeric forms of formulae $I_I$, $I_{II}$, $I_{III}$ and $I_{IV}$, wherein $R_1$, $R_2$ and $R_3$ are as defined for formula I, and the preparation of mixtures of those stereoisomeric forms in any ratio.

The process according to the invention is suitable preferably for the preparation of compounds of formula I wherein $R_1$ is hydrogen or $C_1$-$C_4$alkyl and $R_2$ and $R_3$ are hydrogen.

The process according to the invention is suitable preferably for the preparation of compounds of formula I wherein $R_1$ is hydrogen or methyl and $R_2$ and $R_3$ are hydrogen.

The process according to the invention is suitable especially for the preparation of compounds of formula I wherein $R_1$, $R_2$ and $R_3$ are hydrogen.

Compounds of formula II wherein X is bromine are preferably used in the process according to the invention.

Compounds of formula II wherein X is chlorine are preferably used in the process according to the invention.

Process Step a):

Palladium complex compounds which are used in process step (a) are formed from a palladium precursor and at least one suitable ligand. In process step (a), the palladium complex complexes are preferably present in dissolved form as palladium-ligand complexes.

In the context of the present invention, palladium complex compounds are expressly understood to include compounds consisting of cyclic organic palladium compounds, the so-called "palladacycles", and secondary phosphines.

The palladium complex compounds may be used as already formed complex compounds in process step (a) or are formed in situ in process step (a).

In order to form palladium complex compounds, a palladium precursor is reacted with at least one suitable ligand. In the event of incomplete reaction, it can be the case that minor amounts of palladium precursor or of ligand do not dissolve in the reaction mixture.

Suitable palladium precursors are palladium acetate, palladium dichloride, palladium dichloride solution, palladium$_2$ (dibenzylidene-acetone)$_3$ or palladium (dibenzylidene-acetone)$_2$, palladium tetrakis(triphenylphosphine), palladium-on-carbon, palladium dichlorobis(benzonitrile), palladium (tris-tert-butylphosphine)$_2$ or a mixture of palladium$_2$ (dibenzylidene-acetone)$_3$ and palladium (tris-tert-butylphosphine)$_2$.

Suitable ligands are tertiary phosphine ligands, N-heterocyclic carbene ligands or phosphinic acid ligands.

In the context of the present invention, tertiary phosphine ligands are sub-divided into monodentate tertiary phosphine ligands and bidentate tertiary phosphine ligands. A "monodentate ligand" is understood to be a ligand able to occupy one co-ordination site of the palladium centre. A "bidentate ligand" is understood to be a ligand which is able to occupy two co-ordination sites of the palladium centre and is accordingly capable of chelating the palladium atom or palladium ion.

Examples of tertiary phosphine ligands are:

(A) monodentate tertiary phosphine ligands:

tri-tert-butyl-phosphine, tri-tert-butyl-phosphonium tetrafluoroborate ("P(tBu)$_3$HBF$_4$"), tris-ortho-tolyl-phosphine ("P(oTol)$_3$"), tris-cyclohexyl-phosphine ("P(Cy)$_3$"), 2-di-tert-butyl-phosphino-1,1'-bisphenyl ("P(tBu)$_2$BiPh"), 2-di-cyclohexyl-phosphino-1,1'-bisphenyl ("P(Cy)$_2$BiPh") or 2-dicyclohexylphosphino-2',4',6'-triisopropyl-1,1'-bisphenyl ("x-Phos"), tert-butyl-di-1-adamantyl-phosphine ("P(tBu)(Adam)$_2$"); or (B) bidentate tertiary phosphine ligands:

(B1) biphosphine ligands:

(B1.1): ferrocenyl biphosphine ligands such as, for example, R(−)-di-tert-butyl-[1-[(S)-2-(dicyclohexylphosphinyl)ferrocenyl]ethyl]phosphine ("Josiphos 1")

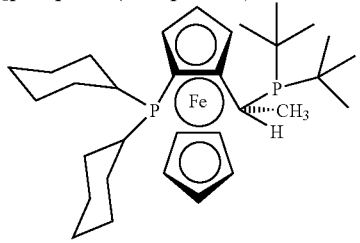

(R)-1-[(S)-2-(dicyclohexyl-phosphino)ferrocenyl]ethyl-di-tert-butylphosphine, racemic di-tert-butyl-[1-[2-(dicyclohexylphosphinyl)ferrocenyl]ethyl]phosphine ("racemic Josiphos 1"), (R)-1-((S)-2-(di-tert-butylphosphino)ferrocenyl)ethyl-di-ortho-tolylphosphine ("Josiphos 2")

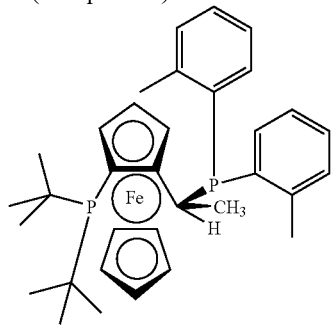

(R)-1-[(S)-2-(di-tert-butyl-phosphino)ferrocenyl]ethyl-di-o-tolylphosphine, racemic 1-(2-(di-tert-butylphosphino)ferrocenyl)ethyl-di-ortho-tolylphosphine ("racemic Josiphos 2"), 1,1'-bis(diphenylphosphino)ferrocene ("dppf"), 1,1'-bis(di-tert-butylphosphino)-ferrocene, R-1-[(S)-2-(diphenylphosphino)ferrocenyl]ethyl-dicyclohexylphosphine, racemic 1-[2-(diphenylphosphino)ferrocenyl]ethyl-dicyclohexylphosphine, R-1-[(S)-2-(2'-diphenylphosphinophenyl]ferrocenyl)ethyl-di-tert-butylphosphine or (B1.2): binaphthyl bisphosphine ligands such as, for example, 2,2'-bis(diphenylphosphino)-1,1'-binaphthyl ("BINAP"), R-(+)-2,2'-bis(di-p-tolylphosphino)-1,1'-binaphthyl ("Tol-BINAP"), racemic 2,2'-bis(di-p-tolylphosphino)-1,1'-binaphthyl ("racemic Tol-BINAP"); or (B1.3): 9,9-dimethyl-4,5-bis(diphenylphosphino)xanthene ("Xantphos"); or (B2) aminophosphine ligands:

(B2.1): biphenyl ligands such as, for example, 2-dicyclohexylphosphino-(N,N-dimethylamino)-1,1'-biphenyl ("PCy$_2$NMe$_2$BiPh")

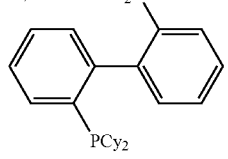

PCy$_2$-NMe$_2$-BiPh 2-dicyclohexylphosphino-(N,N-dimethylamino)-1,1'-biphenyl or 2-di-tert-butylphosphino-(N,N-dimethylamino)-1,1'-biphenyl ("P(tBu)$_2$NMe$_2$BiPh").

Examples of N-heterocyclic carbene ligands are:

1,3-bis(2,6-diisopropylphenyl)imidazolium chloride ("I—Pr")

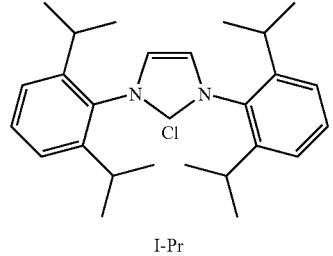

I-Pr 1,3-bis(2,6-diisopropylphenyl)imidazolium chloride, 1,2-bis(1-adamantyl)imidazolium chloride ("I-Ad") or 1,3-bis(2,6-methylphenyl)imidazolium chloride ("I-Me").

An example of a phosphinic acid ligand is:

di-tert-butyl-phosphine oxide.

An example of a palladium complex compound based on a "palladacycle" and secondary phosphine is a compound of formula A-1:

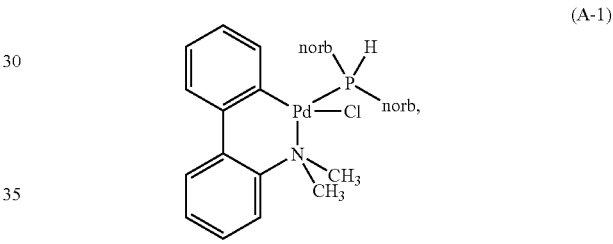

(A-1)

wherein "norb" is norbornyl. Compound A-1 is described in SYNLETT, 2549-2552, 2004 and is given the designation "SK-CC01-A" therein.

A further example of a palladium complex compound based on a "palladacycle" and secondary phosphine is a compound of formula A-2:

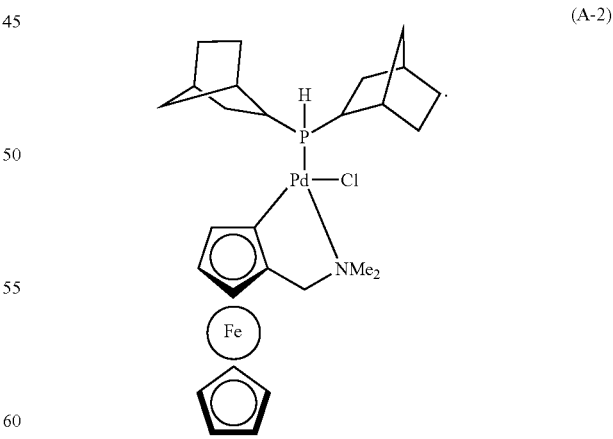

(A-2)

Compound A-2 is described in SYNLETT, 2549-2552, 2004 and is given the designation "SK-CC02-A" therein.

Examples of palladium complex compounds using phosphinic acid ligands are described in Journal of Organic Chemistry, 66, 8677-8681 and are given the designations "POPd", "POPd2" and "POPD1" therein.

Examples of palladium complex compounds using N-heterocyclic carbene ligands are:

naphthoquinone-1,3-bis(2,6-diisopropylphenyl)imidazol-2-ylidene-palladium ("[Pd—NQ-IPr]$_2$")

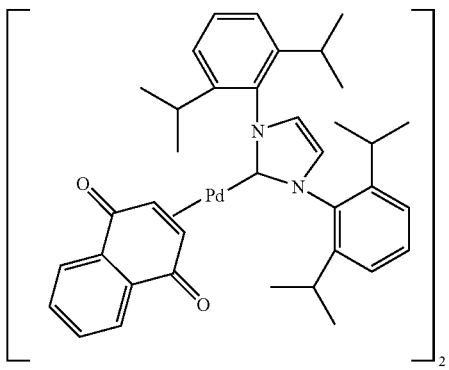

[Pd-NQ-IPr]$_2$
naphthoquinone-1,3-bis-
(2,6-diisopropylphenyl)imidazol-
2-ylidene-palladium, divinyl-tetramethylsiloxane-1,3-bis(2,6-diisopropylphenyl)imidazol-2-ylidene-palladium ("Pd—VTS—IPr")

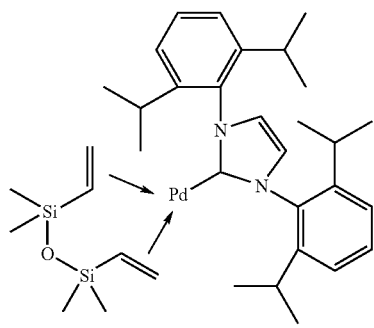

Pd-VTS-IPr
divinyl-tetramethylsiloxane-1,3-bis-
(2,6-diisopropylphenyl)imidazol-
2-ylidene-palladium, 1,3-bis(2,6-diisopropylphenyl)imidazol-2-ylidene-palladium dichloride ("Pd—Cl—IPr"), 1,3-bis(2,6-diisopropylphenyl)imidazol-2-ylidene-palladium diacetate ("Pd—OAc—IPr"), allyl-1,3-bis(2,6-diisopropylphenyl)imidazol-2-ylidene-palladium chloride ("Pd—Al—Cl—IPr") or a compound of formula A-3:

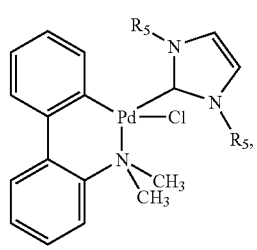

(A-3)

wherein $R_5$ is 2,6-diisopropylphenyl or 2,4,6-trimethylphenyl. [Pd—NQ-IPr]$_2$, Pd—VTS—IPr, Pd—Cl—IPr and Pd—Al—Cl—IPr are described in Organic Letters, 4, 2229-2231, 2002 and in SYNLETT, 275-278, 2005. The compound of formula A-3 is described in Organic Letters, 5, 1479-1482, 2003.

One palladium complex compound or a mixture of palladium complex compounds may be used in the process according to the invention.

For formation of the palladium complex compound, preference is given to the use, as palladium precursor, of palladium acetate, palladium$_2$ (dibenzylidene-acetone)$_3$, palladium (dibenzylidene-acetone)$_2$, palladium dichloride solution or a mixture of palladium$_2$ (dibenzylidene-acetone)$_3$ and palladium (tris-tert-butylphosphine)$_2$. Special preference is given to the use of palladium acetate or palladium dichloride.

At least one ligand is used for formation of the palladium complex compound.

Preference is given to the use of palladium complex compounds which comprise at least one ligand selected from a monodentate tertiary phosphine ligand, a bidentate tertiary phosphine ligand and an N-heterocyclic carbene ligand.

Preference is given to the use of palladium complex compounds which comprise at least one ligand selected from an N-heterocyclic carbene ligand, a monodentate tertiary phosphine ligand and a bidentate tertiary phosphine ligand which is selected from a ferrocenyl biphosphine ligand, a binaphthyl bisphosphine ligand and an aminophosphine ligand.

Preference is given to the use of palladium complex compounds which comprise at least one ligand selected from tri-tert-butyl-phosphine, P(tBu)$_3$HBF$_4$, P(oTol)$_3$, P(Cy)$_3$, P(tBu)$_2$BiPh, P(Cy)$_2$BiPh, x-Phos, P(tBu)(Adam)$_2$, Josiphos 1, racemic Josiphos 1, Josiphos 2, racemic Josiphos 2, dppf, 1,1'-bis(di-tert-butylphosphino)ferrocene, R-1-[(S)-2-(diphenylphosphino)-ferrocenyl]ethyl-dicyclohexylphosphine, racemic 1-[2-(diphenylphosphino)ferrocenyl]ethyl-dicyclohexylphosphine, R-1-[(S)-2-(2'-diphenylphosphinophenyl]ferrocenyl)ethyl-di-tert-butylphosphine, BINAP, Tol-BINAP, racemic Tol-BINAP, Xantphos, PCy$_2$NMe$_2$BiPh, P(tBu)$_2$NMe$_2$BiPh, I—Pr, I-Ad and I-Me, or a palladium complex compound of formula A-3 wherein $R_5$ is 2,6-diisopropylphenyl or 2,4,6-trimethylphenyl.

Preference is given to the use of palladium complex compounds which comprise at least one ligand selected from tri-tert-butyl-phosphine, P(tBu)$_3$HBF$_4$, P(tBu)$_2$BiPh, P(Cy)$_2$BiPh, x-Phos, Josiphos 1, racemic Josiphos 1, Josiphos 2, racemic Josiphos 2, PCy$_2$NMe$_2$BiPh and I—Pr.

Preference is given to the use of palladium complex compounds which comprise at least one ligand selected from tri-tert-butyl-phosphine, P(tBu)$_3$HBF$_4$, P(tBu)$_2$BiPh, P(Cy)$_2$BiPh, x-Phos, PCy$_2$NMe$_2$BiPh and I—Pr.

Preference is given to the use of palladium complex compounds which comprise at least one ligand selected from tri-tert-butyl-phosphine, P(tBu)$_3$HBF$_4$, PCy$_2$NMe$_2$BiPh and I—Pr.

Preference is given to the use of palladium complex compounds which comprise the ligand tri-tert-butyl-phosphine or P(tBu)$_3$HBF$_4$.

Preference is given to the use of palladium complex compounds which comprise the ligand PCy$_2$NMe$_2$BiPh.

Preference is given to the use of palladium complex compounds which comprise the ligand I—Pr.

Preference is given to the use of palladium complex compounds which comprise at least one ligand selected from Josiphos 1 and racemic Josiphos 1.

Preference is given to the use of palladium complex compounds which comprise the ligand racemic Josiphos 1.

Palladium complex compounds, palladium precursors and/or ligands are used in catalytic amounts in the process according to the invention.

Palladium complex compounds are used preferably in a ratio of from 1:10 to 1:10 000 relative to compounds of formula II, especially in a ratio of from 1:100 to 1:1000.

Palladium precursors are used preferably in a ratio of from 1:10 to 1:10 000 relative to compounds of formula II, especially in a ratio of from 1:100 to 1:1000.

Ligands are used preferably in a ratio of from 1:10 to 1:10 000 relative to compounds of formula II, especially in a ratio of from 1:100 to 1:1000.

In the reaction according to the invention, preference is given to the use, as compound of formula III, of a compound of formula III wherein $R_4$ is hydrogen (benzylamine).

Compounds of formula III are preferably used in an equimolar amount or in an excess relative to compounds of formula II. Suitable amounts of compounds of formula III for this reaction are, for example, from 1 to 3 equivalents, especially from 1 to 2 equivalents.

Suitable bases are, for example, alcoholates, e.g. sodium tert-butanolate, potassium tert-butanolate, sodium methanolate or sodium ethanolate, or inorganic bases such as carbonates, e.g. $K_2CO_3$, $Na_2CO_3$ or $Cs_2CO_3$, hydroxides, e.g. NaOH or KOH, or phosphates, e.g. $K_3PO_4$; preference is given to alcoholates and special preference is given to sodium tert-butanolate.

When NaOH or KOH is used as the base, a phase transfer catalyst such as, for example, cetyltrimethylammonium bromide may be used.

Suitable amounts of base for this reaction are, for example, from 1 to 3 equivalents, especially from 1 to 2 equivalents.

The reaction according to the invention may be carried out in an inert solvent.

In one embodiment of the invention, the reaction according to the invention is carried out in an inert solvent. Suitable solvents are, for example, a compound of formula V

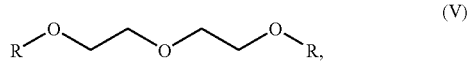

wherein R is $C_1$-$C_6$alkyl, preferably methyl; dimethoxyethane; tert-butyl methyl ether; pentane; hexane; cyclohexane; tetrahydrofuran; dioxane; toluene; xylene or trimethylbenzenes such as, for example, mesitylene; and also mixtures thereof. A preferred solvent is dimethoxyethane or xylene.

In that embodiment, the inert solvent is preferably anhydrous.

In a further embodiment of the invention, the reaction is carried out without solvent. In that embodiment, compounds of formula III are preferably used in an excess relative to compounds of formula II.

The reaction according to the invention is carried out at ambient temperature or at elevated temperature, preferably in a temperature range from 50° C. to 180° C., especially in a temperature range from 50° C. to 100° C.

The reaction according to the invention may be carried out at normal, elevated or reduced pressure. In one embodiment, the reaction according to the invention is carried out at normal pressure.

The reaction time of the reaction according to the invention is generally from 1 to 48 hours, preferably from 4 to 30 hours, especially from 4 to 18 hours.

The reaction according to the invention may be carried out in an inert gas atmosphere. For example, nitrogen or argon is used as inert gas.

In one embodiment of the reaction according to the invention, the reaction is carried out in a nitrogen atmosphere.

Process Step b):

A suitable reducing agent for process step b) is, for example, hydrogen in the presence of a metal catalyst.

Amounts of reducing agent suitable for this reaction are, for example, from 1 to 5 equivalents, especially from 1 to 1.3 equivalents.

Suitable metal catalysts are, for example, palladium catalysts such as, for example, palladium-on-carbon catalysts, or rhodium catalysts; special preference is given to palladium catalysts.

Amounts of metal catalyst suitable for this reaction are catalytic amounts such as, for example, from 0.001 to 0.5 equivalent, especially from 0.01 to 0.1 equivalent.

This reaction is preferably carried out in the presence of an inert solvent. Suitable solvents are, for example, alcohols, e.g. methanol, ethanol, propanol or isopropanol, or aprotic solvents, e.g. tetrahydrofuran, tert-butyl methyl ether, dioxane, ethyl acetate or dimethoxyethane, and also mixtures thereof; special preference is given to tetrahydrofuran.

The temperatures are generally from 0° C. to 80° C.; preference is given to a range from 0° C. to 25° C.; special preference is given to carrying out this reaction at ambient temperature.

The reaction time for this reaction is generally from 1 to 48 hours, preferably from 1 to 6 hours.

The reaction according to the invention may be carried out at normal, elevated or reduced pressure. In one embodiment, the reaction according to the invention is carried out at normal pressure.

If suitable reaction conditions are selected, the compound of formula IV obtained in reaction step a) can be directly reacted to form a compound of formula I without isolating intermediates.

The process according to the invention is very especially suitable for the preparation of compounds of formula I wherein $R_1$, $R_2$ and $R_3$ are each independently of the others hydrogen or $C_1$-$C_4$alkyl, by a) reaction of a compound of formula II, wherein $R_1$, $R_2$ and $R_3$ are each independently of the others hydrogen or $C_1$-$C_4$alkyl and X is chlorine, with benzylamine in the presence of sodium tert-butanolate and catalytic amounts of at least one palladium complex compound, wherein the palladium complex compound comprises at least one ligand selected from tri-tert-butyl-phosphine, tri-tert-butyl-phosphonium tetrafluoroborate, 2-dicyclohexylphosphino-(N,N-dimethylamino)-1,1'-biphenyl and 1,3-bis(2,6-diisopropylphenyl)imidazolium chloride, to form a compound of formula IV, wherein $R_1$, $R_2$, $R_3$ and $R_4$ are each independently of the others hydrogen or $C_1$-$C_4$alkyl, and b) conversion of the latter compound into the compound of formula I using hydrogen in the presence of a metal catalyst.

Compounds of formula I wherein $R_1$ is hydrogen or methyl and $R_2$ and $R_3$ are hydrogen are especially suitable for that embodiment.

Compounds of formula I wherein $R_1$, $R_2$ and $R_3$ are hydrogen are very especially suitable for that embodiment.

The compounds of formula II wherein X is bromine are generally known and can be prepared according to the processes described in WO 03/074491.

The compounds of formula II wherein X is chlorine can be prepared in analogous manner to the processes described in WO 03/074491 for the corresponding compounds of formula II wherein X is bromine. For example, the compound of formula II wherein $R_1$, $R_2$ and $R_3$ are hydrogen and X is chlorine (compound no. B1) can be prepared as shown in Reaction Scheme 1 and as explained by Examples A1-A3 which follow:

Scheme 2:

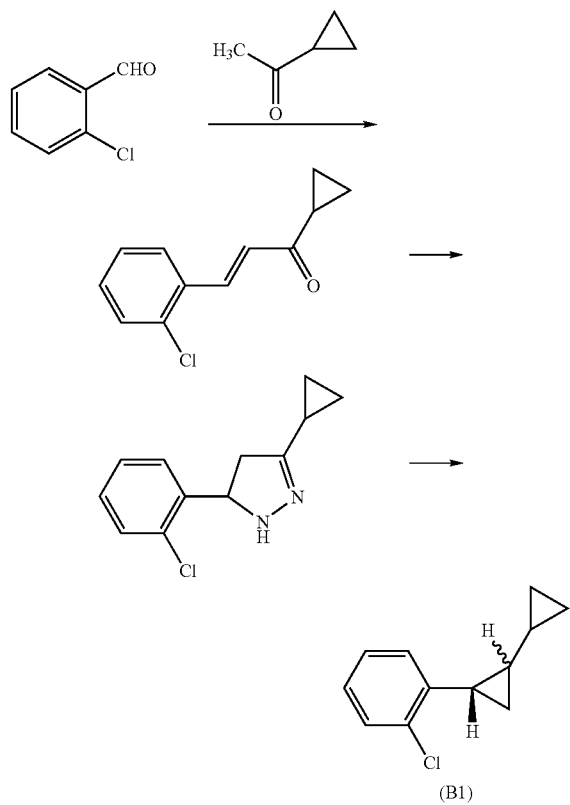

(B1)

PREPARATION EXAMPLE A1

Preparation of 3-(2-chlorophenyl)-1-cyclopropyl-propenone 67 g of 30% sodium hydroxide solution are mixed with 350 ml of water and 97.5 g (1.1 mol) of cyclopropyl methyl ketone and heated to 90° C., with stirring. 143.5 g (1 mol) of 2-chloro-benzaldehyde are added dropwise to the resulting mixture and stirring is carried out for 5 hours. During stirring, after 2 hours and after a further 3 hours, 2 ml of cyclopropyl methyl ketone are added on each occasion. After a total reaction time of 6 hours, cooling to 50° C. is carried out. The reaction mixture is filtered and the phases are separated. The organic phase is concentrated. 188.6 g of 3-(2-chlorophenyl)-1-cyclopropyl-propenone are obtained in the form of a yellow oil.

$^1$H NMR (CDCl$_3$): 0.95-1.04 (m, 2H); 1.16-1.23 (m, 2H); 2.29-2.37 (m, 1H); 6.83 (d, J=15 Hz); 7.27-7.35 (m, 2H); 7.40-7.47 (m, 1H); 8.03 (d, J=15 Hz)

PREPARATION EXAMPLE A2

Preparation of 5-(2-chlorophenyl)-3-cyclopropyl-4, 5-dihydro-1H-pyrazole 250 g of ethanol are added to 188.6 g of the 3-(2-chlorophenyl)-1-cyclopropyl-propenone (1 mol) prepared according to A1. 53 g (1.05 mol) of hydrazine hydrate are added dropwise at 20° C., with stirring. The reaction mixture is stirred at 70° C. for 2 hours. The reaction mixture is then cooled to 50° C. A mixture of 5.5 g of oxalic acid dihydrate (0.044 mol) and 20 g of ethanol is added, whereupon a solid precipitates out. The reaction mixture is cooled to 25° C. and is filtered through a sintered-glass suction filter and washed with 50 g of ethanol. A yellow filtrate is obtained, which is concentrated by evaporation using a rotary evaporator at 60° C. and down to 20 mbar to form a yellow oil. 201.5 g of an isomeric mixture having the main component 5-(2-chlorophenyl)-3-cyclopropyl-4,5-dihydro-1H-pyrazole are obtained in the form of a yellow oil.

PREPARATION EXAMPLE A3

Synthesis of 2-(2-chlorophenyl)bicyclopropyl

To a solution of 50 g (0.36 mol) of potassium carbonate in 600 g of ethylene glycol there are added at 190° C., in the course of 2 hours, 201.5 g of 5-(2-chlorophenyl)-3-cyclopropyl-4,5-dihydro-1H-pyrazole, prepared as described under A2. Stirring is then carried out for 2 hours at 190° C. The end of the reaction is indicated by cessation of the evolution of gas. The reaction mixture is then cooled to 100° C., whereupon phase separation occurs and the upper, product phase is separated off. 158 g of 2-(2-chlorophenyl)bicyclopropyl are obtained as crude product, which may be further purified, for example by distillation.

$^1$H NMR (CDCl$_3$): 0.0-1.13 (m, 8H); 1.95-2.02 (m, 0.63H, trans isomer) and 2.14-2.22 (m, 0.37H, cis isomer); 6.88-6.94 (m); 7.05-7.24 (m); 7.31-7.42 (m)

Palladium complex compounds, palladium precursors and ligands as used in process step (a) are generally known and, for the most part, commercially available.

The compounds of formula IV are valuable intermediates for the preparation of compounds of formula I and have been developed specifically for the present process according to the invention. The present invention accordingly relates also thereto.

The present invention will be explained in greater detail using the following Examples:

EXAMPLE P1

Preparation of benzyl(2-bicyclopropyl-2-yl-phenyl)amine 3 g of 2-(2-chlorophenyl)bicyclopropyl (15.6 mmol, trans/cis ratio of about 2:1), 2.5 g of benzylamine (23.4 mmol), 2.4 g of sodium tert-butanolate (25 mmol), 35 mg of Pd(II) acetate (0.16 mmol) and 60 mg of R(−)-di-tert-butyl-[1-[(S)-2-(dicyclohexylphosphanyl)-ferrocenyl]ethyl]phosphine (0.11 mmol) are dissolved in 30 ml of dimethoxyethane. The reaction mixture is heated to the reflux temperature of the solvent and is stirred for 24 hours. After cooling, ethyl acetate is added and the organic phase is washed with water. The solvent is removed using a water jet vacuum and the residue is dried. The product is purified by column chromatography on silica gel (eluant:ethyl acetate/hexane 1:15). 3.58 g of benzyl(2-bicyclopropyl-2-yl-phenyl)amine (87% of theory) are obtained in the form of a brown oil (trans/cis ratio of about 2:1).

EXAMPLE P2

Preparation of benzyl(2-bicyclopropyl-2-yl-phenyl)amine 3.7 g of 2-(2-bromophenyl)bicyclopropyl (15.6 mmol, trans/cis ratio of about 3:1), 2.0 g of benzylamine (18.7 mmol), 2.1 g of sodium tert-butanolate (21.8 mmol), 3.5 mg of Pd(II) acetate (0.016 mmol) and 8.6 mg of R(−)-di-tert-butyl-[1-[(S)-2-(dicyclohexylphosphanyl)-ferrocenyl]ethyl]phosphine (0.016 mmol) are dissolved in 30 ml of dimethoxyethane. The reaction mixture is heated to 70° C. and stirred for 24 hours. After cooling, ethyl acetate is added. The organic phase is washed with water. The solvent is removed using a water jet vacuum and the residue is dried. The product is purified by column chromatography on silica gel (eluant: ethyl acetate/hexane 1:15). 3.47 g of benzyl(2-bicyclopropyl-2-yl-phenyl)amine (84% of theory) are obtained in the form of a brown oil (trans/cis ratio of about 3:1).

EXAMPLE P3

Preparation of 2-bicyclopropyl-2-yl-phenylamine 1 g of benzyl(2-bicyclopropyl-2-yl-phenyl)amine (3.8 mmol, trans/cis ratio of about 3:1) is dissolved in 15 ml of absolute tetrahydrofuran. Then 50 mg of Pd (5%) on activated carbon are added. Hydrogenation is then carried out, with stirring, for 1 hour at room temperature. After completion of the reaction, the catalyst is filtered off and the solvent is removed using a water jet vacuum. The product is purified by chromatography on silica gel (eluant:ethyl acetate/hexane 1/15). 0.61 g of 2-bicyclopropyl-2-ylphenylamine (92% of theory) is obtained in the form of a brownish liquid (trans/cis ratio of about 3:1).

Using the above Examples, the following compounds of formula I can be prepared:

TABLE 1

Compounds of formula I

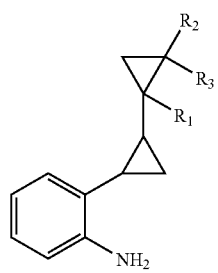

(I)

| Comp. no. | $R_1$ | $R_2$ | $R_3$ |
|---|---|---|---|
| A1 | H | H | H |
| A2 | $CH_3$ | H | H |
| A3 | H | $CH_3$ | H |
| A4 | H | H | $CH_3$ |
| A5 | $CH_3$ | $CH_3$ | H |
| A6 | $CH_3$ | H | $CH_3$ |
| A7 | H | $CH_3$ | $CH_3$ |
| A8 | $CH_3$ | $CH_3$ | $CH_3$ |

The following compounds of formula II are suitable for use in the process according to the invention:

TABLE 2

Compounds of formula II

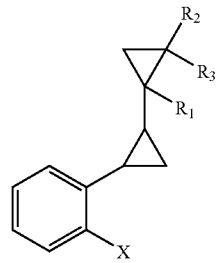

(II)

| Comp. no. | X | $R_1$ | $R_2$ | $R_3$ |
|---|---|---|---|---|
| B1 | Cl | H | H | H |
| B2 | Cl | $CH_3$ | H | H |
| B3 | Cl | H | $CH_3$ | H |
| B4 | Cl | H | H | $CH_3$ |
| B5 | Cl | $CH_3$ | $CH_3$ | H |
| B6 | Cl | $CH_3$ | H | $CH_3$ |
| B7 | Cl | H | $CH_3$ | $CH_3$ |
| B8 | Cl | $CH_3$ | $CH_3$ | $CH_3$ |
| B9 | Br | H | H | H |
| B10 | Br | $CH_3$ | H | H |
| B11 | Br | H | $CH_3$ | H |
| B12 | Br | H | H | $CH_3$ |
| B13 | Br | $CH_3$ | $CH_3$ | H |
| B14 | Br | $CH_3$ | H | $CH_3$ |
| B15 | Br | H | $CH_3$ | $CH_3$ |
| B16 | Br | $CH_3$ | $CH_3$ | $CH_3$ |

Suitable intermediates for the preparation of compounds of formula I are described in Table 3:

TABLE 3

Intermediates of formula IV

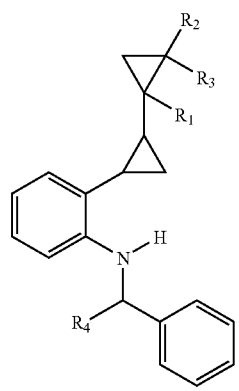

(IV)

| Comp. no. | $R_1$ | $R_2$ | $R_3$ | $R_4$ |
|---|---|---|---|---|
| C1 | H | H | H | H |
| C2 | $CH_3$ | H | H | H |
| C3 | H | $CH_3$ | H | H |
| C4 | H | H | $CH_3$ | H |
| C5 | $CH_3$ | $CH_3$ | H | H |
| C6 | $CH_3$ | H | $CH_3$ | H |
| C7 | H | $CH_3$ | $CH_3$ | H |
| C8 | $CH_3$ | $CH_3$ | $CH_3$ | H |
| C9 | H | H | H | $CH_3$ |
| C10 | $CH_3$ | H | H | $CH_3$ |

TABLE 3-continued

| C11 | H | CH$_3$ | H | CH$_3$ |
| C12 | H | H | CH$_3$ | CH$_3$ |

As a result of the provision of the present invention, it is possible to aminate ortho-bicyclopropyl-substituted halobenzenes in high yields and with little outlay.

The starting compounds of the process of the present invention are distinguished by being readily accessible and easily handled and, in addition, they are economically priced.

In a preferred embodiment of the process according to the invention, the palladium used in the process is recycled. This embodiment constitutes a variant of the process according to the invention which is especially interesting from an economic point of view.

In a preferred embodiment of the invention, compounds of formula II wherein X is chlorine are used. The starting compounds of this preferred embodiment of the process of the invention are distinguished by being especially readily accessible and by their especially economical price. This embodiment accordingly constitutes a variant of the process of the process according to the invention which is especially interesting from an economic point of view.

It is known, however, that, under the conditions of palladium-catalysed cross-coupling, this class of starting compounds, the deactivated chlorobenzene substrates, are especially difficult to aminate because of the extremely low reactivity of the chlorine leaving group, compared to deactivated bromobenzene substrates.

In addition, the yield is generally further reduced when using a primary alkylamine nucleophile having a hydrogen atom in the β position such as, for example, the compounds of formula III. This is due, firstly, to the subsidiary reaction of β elimination within the alkylamine nucleophile to form the imine, an unsubstituted aryl being formed from the aryl halide substrate. Secondly, when using primary amine nucleophiles it is also necessary to take into account the follow-on reaction of further amination to the secondary arylamine, which can reduce the yield of the desired primary arylamines.

The amination of deactivated, electron-rich chlorobenzene substrates with primary alkylamine nucleophiles which have a hydrogen atom in the β position is therefore regarded as being extremely difficult because of the reduced reactivity and because of the subsidiary and follow-on reactions. Those difficulties are pointed out, for example, in the above-mentioned summary articles.

It has been found, surprisingly, that palladium complex compounds having at least one ligand selected from an N-heterocyclic carbene ligand, a monodentate tertiary phosphine ligand and a bidentate tertiary phosphine ligand which is selected from a ferrocenyl biphosphine ligand and an aminophosphine ligand are especially suitable for the amination of compounds of formula II wherein X is chlorine.

For that reason, for the formation of the palladium complex compound preference is given to the use of at least one ligand selected from an N-heterocyclic carbene ligand, a monodentate tertiary phosphine ligand and a bidentate tertiary phosphine ligand which is selected from a ferrocenyl biphosphine ligand and an aminophosphine ligand.

Preference is given to the use of palladium complex compounds which comprise at least one ligand selected from tri-tert-butyl-phosphine, P(tBu)$_3$HBF$_4$, P(tBu)$_2$BiPh, P(Cy)$_2$BiPh, x-Phos, Josiphos 1, racemic Josiphos 1, Josiphos 2, racemic Josiphos 2, PCy$_2$NMe$_2$BiPh and I—Pr.

Tables 4 and 5 describe yields of the amination reaction of chlorobenzenes.

TABLE 4

Yields of the amination reaction of chlorobenzenes

| Palladium precursor | mol % | Ligand | mol % | Yield |
|---|---|---|---|---|
| Pd(OAc)$_2$ | 1 | P(tBu)$_3$HBF$_4$ | 0.69 | 86% |
| Pd(OAc)$_2$ | 1 | P(tBu)$_2$BiPh | 0.69 | 86% |
| Pd(OAc)$_2$ | 1 | x-Phos | 0.69 | 92% |
| Pd(OAc)$_2$ | 1 | Josiphos 1 | 0.69 | 92% |
| Pd(OAc)$_2$ | 1 | Josiphos 2 | 0.69 | 90% |
| Pd(OAc)$_2$ | 1 | PCy$_2$NMe$_2$BiPh | 0.69 | 98% |
| Pd(OAc)$_2$ | 1 | I—Pr | 0.69 | 96% |

A mixture of 100 mg of 2-(2-chlorophenyl)bicyclopropyl (0.5 mmol), 0.085 ml of benzylamine (0.78 mmol), 8 mg of sodium tert-butanolate (0.83 mmol, 1.2 mg of Pd(II) acetate (0.005 mmol, 1 mol %) and 0.0035 mmol (0.69 mol %) of ligand is prepared. 3 ml of dimethoxyethane are added and stirring is carried out at 90° C. for 16 hours. After cooling, 2.5 ml of ethyl acetate and 3 ml of water are added and the organic phase is extracted. The identity of the reaction product benzyl(2-bicyclopropyl-2-yl-phenyl)amine and its yield are determined by means of gas chromatography.

TABLE 5

Yields of the amination reaction of chlorobenzenes

| Palladium complex compound | mol % | Yield |
|---|---|---|
| Pd—Al—Cl—(I—Pr) | 1 | 96% |
| Pd-VTS-(I—Pr) | 1 | 96% |
| [Pd-NQ-I—Pr]$_2$ | 2 | 97% |
| [Pd-NQ-I—Pr]$_2$ | 0.4 | 95% |

A mixture of 100 mg of 2-(2-chlorophenyl)bicyclopropyl (0.5 mmol), 0.085 ml of benzylamine (0.78 mmol), 8 mg of sodium tert-butanolate (0.83 mmol) and palladium complex compound in the desired palladium complex compound concentration is produced. The palladium complex compounds are prepared using processes known from the literature and are added as already formed palladium complex compounds directly to the reaction mixture. 3 ml of dimethoxyethane are added and stirring is carried out at 90° C. for 16 hours. After cooling, 2.5 ml of ethyl acetate and 3 ml of water are added and the organic phase is extracted. The identity of the reaction product benzyl(2-bicyclopropyl-2-yl-phenyl)amine and its yield are determined by means of gas chromatography.

In an especially preferred embodiment of the invention, there are used palladium complex compounds having at least one ligand selected from an N-heterocyclic carbene ligand, a monodentate tertiary phosphine ligand and a bidentate aminophosphine ligand.

In this especially preferred embodiment of the invention, compounds of formula II wherein X is chlorine can be reacted with small amounts of palladium complex compounds whilst maintaining high yields. As a result, the costs for the catalyst are substantially reduced. This embodiment accordingly constitutes a variant of the process according to the invention which is very especially interesting from an economic point of view.

This especially preferred embodiment of the present invention makes it possible to use ligands in a ratio of from 1:10 000 to 1:200 relative to compounds of formula II (or from 0.01 mol % to 0.5 mol % in relation to compounds of formula II), whilst maintaining high yields.

In Angewandte Chemie International Edition, 44, 1371-1375, 2005, it is described that Josiphos 1 is suitable as a ligand for reactions of ortho-methyl-substituted chlorobenzenes, using the ligand in a range of from 1:1000 to 1:10 000 relative to compounds of formula II. Yields of 97% when using Josiphos 1 in a ratio of 1:1000 relative to compounds of formula II and of 98% when using Josiphos 1 in a ratio of 1:10 000 are described therein. The mentioned reactions were carried out in a glovebox under a nitrogen atmosphere. A reaction in a glovebox points to extremely sensitive reactants/catalysts. For large-scale production operations, as are generally necessary in agrochemistry, glovebox processes do not constitute economically viable preparation processes.

It was moreover found that this property of the ligand Josiphos 1 which was found in the glovebox process cannot be readily transferred from the ortho-methyl-substituted chlorobenzenes to ortho-bicyclopropyl-substituted chlorobenzenes. Instead it was found, when using Josiphos 1, even at amounts of ligand of 1:700 relative to compounds of formula II, that the yield is reduced to 39% (see Table 6). Similar yields were also found when using Josiphos 2.

It has been found, surprisingly, that some palladium complex compounds are especially suitable for this embodiment of the present invention (see Tables 6 and 7).

TABLE 6

Amination reaction yields with a reduced amount of ligand

| Palladium precursor | mol % | Ligand | mol % | Yield |
|---|---|---|---|---|
| Pd(OAc)$_2$ | 0.2 | PCy$_2$NMe$_2$BiPh | 0.14 | 81% |
| Pd(OAc)$_2$ | 0.2 | Josiphos 1 | 0.14 | 39% |
| Pd(OAc)$_2$ | 0.2 | Josiphos 2 | 0.14 | 28% |

A mixture of 100 mg of 2-(2-chlorophenyl)bicyclopropyl (0.5 mmol), 0.085 ml of benzylamine (0.78 mmol), 8 mg of sodium tert-butanolate (0.83 mmol), 0.24 mg of Pd(II) acetate (0.001 mmol, 0.2 mol %) and 0.0007 mmol (0.14 mol %) of ligand is produced. 3 ml of dimethoxyethane are added and stirring is carried out at 90° C. for 16 hours. After cooling, 2.5 ml of ethyl acetate and 3 ml of water are added and the organic phase is extracted. The identity of the reaction product benzyl(2-bicyclopropyl-2-yl-phenyl)amine and its yield are determined by means of gas chromatography.

TABLE 7

Amination reaction yields with a reduced amount of ligand

| Palladium complex compound | mol % | Yield |
|---|---|---|
| [Pd-NQ-I—Pr]$_2$ | 0.2 | 90% |

A mixture of 100 mg of 2-(2-chlorophenyl)bicyclopropyl (0.5 mmol), 0.085 ml of benzylamine (0.78 mmol), 8 mg of sodium tert-butanolate (0.83 mmol) and palladium complex compound in the desired palladium complex compound concentration is produced. The palladium complex compounds are prepared using processes known from the literature and are added as already formed palladium complex compounds directly to the reaction mixture. 3 ml of dimethoxyethane are added and stirring is carried out at 90° C. for 16 hours. After cooling, 2.5 ml of ethyl acetate and 3 ml of water are added and the organic phase is extracted. The identity of the reaction product benzyl(2-bicyclopropyl-2-yl-phenyl)amine and its yield are determined by means of gas chromatography.

Preference is given to the use of palladium complex compounds which comprise at least one ligand selected from tri-tert-butyl-phosphine, P(tBu)$_3$HBF$_4$, PCy$_2$NMe$_2$BiPh and I—Pr.

Preference is given to the use of palladium complex compounds which comprise at least one ligand selected from PCy$_2$NMe$_2$BiPh and I—Pr.

Preference is given to the use of palladium complex compounds which comprise the ligand tri-tert-butyl-phosphine or P(tBu)$_3$HBF$_4$.

Preference is given to the use of palladium complex compounds which comprise the ligand PCy$_2$NMe$_2$BiPh.

Preference is given to the use of palladium complex compounds which comprise the ligand I—Pr.

Preference is given to the use of a compound selected from Pd—Al—Cl—I—Pr, Pd—VTS—I—Pr and [Pd—NQ-I—Pr]$_2$ as palladium complex compound.

Preference is given to the use of [Pd—NQ-I—Pr]$_2$ or Pd—VTS—(I—Pr) as palladium complex compound.

Preference is given to the use of [Pd—NQ-I—Pr]$_2$ as palladium complex compound.

In this especially preferred embodiment, ligands are used preferably in a ratio of from 1:10 000 to 1:200 relative to compounds of formula II, especially in a ratio of from 1:1000 to 1:200 and very especially in a ratio of from 1:700 to 1:500.

The ortho-bicyclopropyl-substituted anilines prepared by the process according to the invention may be used in the preparation of fungicides such as are described, for example, in WO 03/074491. In the course of preparation of an aniline of formula I wherein R$_1$, R$_2$ and R$_3$ are hydrogen (compound no. A1), using the process according to the invention, the by-products of formula IA (compound no. C1) and of formula IB may be formed and may accordingly also be present in certain amounts in the form of impurities in the desired final product:

By-product IA is formed on carrying out reaction step a); by-product IB may be formed on carrying out reaction step b).

When an aniline no. A1 prepared according to the invention is used in the preparation of the fungicide IC by methods such as are described, for example, in WO 03/074491, the impurities ID and IE may therefore be present in the desired fungicide of formula IC:

What is claimed is:

1. A process for the preparation of a compound of formula I (I)

wherein $R_1$, $R_2$ and $R_3$ are each independently of the others hydrogen or $C_1$-$C_4$alkyl, which comprises a) reacting a compound of formula II (II)

wherein $R_1$, $R_2$ and $R_3$ are as defined for formula I and X is bromine or chlorine, with a compound of formula III (III)

wherein $R_4$ is hydrogen or $C_1$-$C_4$alkyl, in the presence of a base and catalytic amounts of at least one palladium complex compound, to form a compound of formula IV (IV)

wherein $R_1$, $R_2$ and $R_3$ are as defined for formula I and $R_4$ is as defined for formula III; and b) converting that compound, using a reducing agent, into the compound of formula I.

2. A process according to claim 1, wherein X is chlorine.

3. A process according to claim 2, wherein the palladium complex compound comprises at least one ligand selected from a monodentate tertiary phosphine ligand, a bidentate tertiary phosphine ligand and an N-heterocyclic carbene ligand.

4. A process according to claim 2, wherein the palladium complex compound comprises at least one ligand selected from tri-tert-butyl-phosphine, tri-tert-butyl-phosphonium tetrafluoroborate, tris-ortho-tolyl-phosphine, tris-cyclohexyl-phosphine, 2-di-tert-butylphosphino-1,1'-bisphenyl, 2-dicyclohexylphosphino-2',4',6'-triisopropyl-1,1'-bisphenyl, R(−)-di-tert-butyl-[1-[(S)-2-(dicyclohexylphosphinyl)ferrocenyl]ethyl] phosphine, racemic di-tert-butyl[1-[2-(dicyclohexylphosphinyl)ferrocenyl]ethyl]phosphine, (R)-1-((S)-2-(di-tert-butylphosphino)ferrocenyl)ethyl-di-ortho-tolylphosphine, racemic 1-(2-(di-tert-butylphosphino)ferrocenyl)ethyl-di-ortho-tolylphosphine, 1,1'-bis(diphenylphosphino)ferrocene, 1,1'-bis(di-tertbutylphosphino)ferrocene, R-1-[(S)-2-(diphenylphosphino)ferrocenyl]ethyl-dicyclohexylphosphine, racemic 1-[2-(diphenylphosphino)ferrocenyl]ethyl-dicyclohexylphosphine, 2,2'bis(diphenylphosphino)-1,1'-binaphthyl, R-(+)-2,2'-bis(di-p-tolylphosphino)-1,1'-binaphthyl, racemic 2,2'-bis(di-p-tolylphosphino)-1,1'-binaphthyl, 9,9-dimethyl-4,5-bis(diphenylphosphino)xanthene, 2-dicyclohexylphosphino-(N,N-dimethylamino)-1,1'-biphenyl, 1,3-bis(2,6-diisopropylphenyl)imidazolium chloride, 1,2-bis(1-adamantyl)imidazolium chloride, tert-butyl-di-1-adamantylphosphine, R-1-[(S)-2-(2'-diphenylphosphinophenyl]ferrocenyl)ethyl-di-tert-butylphosphine, 2-di-tert-butylphosphino-(N,N-dimethylamino)-1,1'-biphenyl and 1,3-bis(2,6-methylphenyl)-imidazolium chloride or wherein the palladium complex compound is a compound of formula A-3

(A-3)

wherein $R_5$ is 2,6-diisopropylphenyl or 2,4,6-trimethylphenyl.

5. A process according to claim 2, wherein the palladium complex compound comprises at least one ligand selected from tri-tert-butyl-phosphine, tri-tert-butyl-phosphonium tetrafluoroborate, 2-dicyclohexylphosphino-(N,N-dimethylamino)-1,1'-biphenyl and 1,3-bis(2,6-diisopropylphenyl) imidazolium chloride.

6. A process according to claim 2, wherein the palladium complex compound comprises at least one ligand selected from 2-dicyclohexylphosphino-(N,N-dimethylamino)-1,1'-biphenyl and 1,3-bis(2,6-diisopropylphenyl)imidazolium chloride.

7. A process according to claim 2, wherein the palladium complex compound comprises at least 1,3-bis(2,6-diisopropylphenyl)imidazolium chloride.

8. A process according to claim 2, wherein the palladium complex compound is a compound selected from naphthoquinone-1,3-bis(2,6-diisopropylphenyl)imidazol-2-ylidene-palladium, divinyl-tetramethylsiloxane-1,3-bis(2,6-diisopropylphenyl)imidazol-2-ylidene-palladium, 1,3-bis(2,6-diisopropylphenyl)imidazol-2-ylidene-palladium dichloride and 1,3-bis(2,6-diisopropylphenyl)imidazol-2-ylidene-palladium diacetate.

9. A process according to claim 2, wherein the palladium complex compound is naphthoquinone-1,3-bis(2,6-diisopropylphenyl)imidazol-2-ylidene-palladium.

10. A process according to claim 5, wherein the ligand is used in a ratio of from 0.01 mol % to 0.5 mol % in relation to the compound of formula II.

11. A compound of formula IV

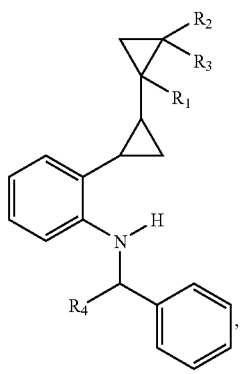

(IV)

wherein $R_1$, $R_2$, $R_3$ and $R_4$ are each independently of the others hydrogen or $C_1$-$C_4$alkyl.

12. A compound of formula IV according to claim 11, wherein R4 is hydrogen.

* * * * *